United States Patent [19]

Wai-Chiu et al.

[11] Patent Number: 5,468,286

[45] Date of Patent: Nov. 21, 1995

[54] ENZYMATICALLY DEBRANCHED STARCHES AS TABLET EXCIPIENTS

[75] Inventors: Chung Wai-Chiu, Westfield; James J. Kasica, Whitehouse Station, both of N.J.

[73] Assignee: National Starch and Chemical Investment Holding Corporation, Wilmington, Del.

[21] Appl. No.: 316,664

[22] Filed: Sep. 30, 1994

[51] Int. Cl.⁶ .................................. C09D 103/02; C08L 3/02
[52] U.S. Cl. ........................ 106/210; 106/213; 106/214; 435/98; 424/450
[58] Field of Search ................................. 106/210, 213, 106/214; 435/98; 424/450

[56] References Cited

U.S. PATENT DOCUMENTS

| | | | |
|---|---|---|---|
| 3,490,742 | 1/1970 | Nichols et al. | |
| 3,532,602 | 10/1970 | Seidman | 435/98 |
| 3,622,677 | 11/1971 | Short et al. | 424/361 |
| 3,632,475 | 1/1972 | Sugimoto et al. | 435/98 |
| 3,721,605 | 3/1973 | Yoshida et al. | 435/98 |
| 3,728,140 | 4/1973 | Yoshida | 106/210 |
| 3,729,380 | 4/1973 | Sugimoto et al. | 195/31 R |
| 3,730,840 | 5/1973 | Sugimoto et al. | 195/31 R |
| 3,734,760 | 5/1973 | Hijiya et al. | 106/213 |
| 3,878,212 | 4/1975 | Yoshida et al. | 106/213 |
| 3,881,991 | 5/1975 | Kurimoto et al. | 195/31 R |
| 4,072,535 | 2/1978 | Short et al. | 106/210 |
| 4,384,005 | 5/1983 | McSweeney | 426/250 |
| 4,551,177 | 11/1985 | Trubiano et al. | 106/210 |
| 4,560,651 | 12/1985 | Nielsen et al. | 435/95 |
| 4,886,678 | 12/1989 | Chiu et al. | 426/578 |
| 4,937,091 | 6/1990 | Zallie et al. | 426/582 |
| 4,971,723 | 11/1990 | Chiu | 252/315.3 |

FOREIGN PATENT DOCUMENTS

| | | |
|---|---|---|
| 386839 | 10/1988 | Austria . |
| 053580 | 6/1982 | European Pat. Off. . |
| 0159631 | 10/1985 | European Pat. Off. . |
| 0343993 | 11/1989 | European Pat. Off. . |
| 0390960 | 10/1990 | European Pat. Off. . |
| 1559081 | 1/1969 | France . |
| 48-37817 | 11/1973 | Japan . |
| 49-80227 | 8/1974 | Japan . |
| 51-28700 | 8/1976 | Japan . |

OTHER PUBLICATIONS

Paselli SA2, Avebe Veendam–Hollard, Product Information Bulletin Feb. 1983.

"Biotechnology at the Leatherhead Food RA", (Jun. 1988), vol. 22, No. 6.

H. F. Zobel, "Starch Crystal Transformations and Their Industrial Importance", Lecture at Detmold (Apr. 23 to 25, 1986).

J. Herman et al.: "Modified Starches as Hydrophilic Matrixes for Controlled Oral Delivery. II. In Vitro Drug Release Evaluation of Thermally Modified Starches", CHEMICAL ABSTRACTS, vol. 112, No. 4, Columbis, Ohio (1990).

Pfannemuller et al.: "Studies on Enzymatically Modified Branched Polysaccharides", Part II: Star–Shaped Polymers from Glycogen and Amylopectin as Structure Models For Starch. Die Starke, vol. 29 (Mar. 1977), No. 3, pp. 73–80.

S. Nanbu et al.: "Estimation of the amylose components of starch and effect of the debranching enzyme on amylose contents", Chemical Abstracts, vol. 82, No. 15 (14th Apr. 1975), p. 464, Columbus, Ohio.

*Primary Examiner*—David Brunsman
*Attorney, Agent, or Firm*—Ellen T. Dec

[57] ABSTRACT

A process for preparing a tablet excipient, comprising the steps:

(a) enzymatically treating a starch containing greater than 90% amylopectin with an alpha-1,6-D-glucanohydrolase to debranch the starch and yield a mixture comprising a starch component selected from the group consisting of amylopectin, partially debranched amylopectin, and a combination thereof, and at least 20%, by weight, of a short chain amylose of from about 5 to 65 anhydroglucose units linked by alpha-1,4-D-glucoside bonds; and (b) drying the starch mixture, wherein the starch mixture is characterized by sufficient compressibility for use as an excipient, a binder, a binder-disintegrant, a binder-diluent, a filler or diluent, a moisture absorbent, a glidant, lubricant or flow agent, a surface gloss or hardness agent, or a combination thereof, in tablets.

11 Claims, No Drawings

ENZYMATICALLY DEBRANCHED
STARCHES AS TABLET EXCIPIENTS

BACKGROUND OF THE INVENTION

This invention relates to a tablet excipient, and in particular, to a starch binder and/or filler useful in manufacturing tablets, pellets, capsules or granules for the delivery of drugs, chemicals or other active agents. The tablet excipient is prepared by the enzymatic debranching of starch containing greater than 90% amylopectin with an alpha-1,6-D-glucanohydrolase to yield at least 20%, by weight, short chain amylose. The starch may be highly or partially debranched and may comprise amylopectin, partially debranched amylopectin, or a combination thereof, in addition to the short chain amylose and will be substantially free of long chain amylose.

Tablets and capsules usually consist of several inert materials, referred to as excipients, in addition to the active ingredient which is present in amounts sufficient to accomplish the desired pharmaceutical, nutritive, or chemical effect. These excipients are generally classified according to their functions, such as diluents (also called bulking agents and fillers), binders which hold the ingredients together, and binder-diluents which perform both functions. Tablets may also contain disintegrants which help the tablet to break apart and release the active ingredient when placed in a fluid environment, lubricants to improve the release of the compressed tablet from the die and punches, glidants to improve the flow, and anti-adhesives to prevent film formation on the punches. Other optional ingredients may be moisture absorbants, surface gloss and/or hardness agents, dyes, flavors, sweeteners, antioxidants and/or sorbents.

Different properties are required from starch used as a binder and starch used as a disintegrant. The most important property required in a binder is compressibility. Granular starches and conventional pregelatinized starches (i.e., cooked and cold-water-dispersible) do not bind well under direct compression.

Tabletting and some capsule-filling operations are based on the ability of certain powders to bind under compression. Compressed tablets may be prepared by wet granulation, dry granulation (e.g., slugging), or direct compression. Common dry dosage capsule-filling operations make use of a material that can be gravity- or force-fed into the capsule or a material that can be formed into a plug which is then used to fill the capsule. For the former, a material which improves the flow properties of the powder mix is desirable. For the latter, a binder-diluent which is easily compressed under low pressure to form a soft plug is required. Because different functional properties are required for these different operations, a starch-based excipient may not be useful in all operations or may serve different purposes in different operations.

The steps involved in a typical wet granulation include mixing the components, preparing the granulating binder solution, thoroughly mixing the components with the granulating binder solution to form a dough, coarse screening the moist mass through a sieve, drying, grinding, adding the lubricant, and compressing the tablets.

The steps involved in slugging are mixing the powdered components, compressing the mixture into hard slugs, grinding the slugs to the desired particle size, screening, adding the other excipients, and compressing the mixture into tablets.

The most preferred and economical tabletting method, direct compression, requires only two steps-mixing the dry components and compressing the mixture into tablets.

The binders or binder-diluents used in the above tabletting or capsule-filling operations should be stable, non-reactive and non-hygroscopic, free-flowing powders with some compressibility. The binders used for direct compression tabletting require excellent binding properties.

Typical wet granulation binders include starch pastes, conventional pregelatinized starches, gelatin, polyvinylpyrrolidone, methyl cellulose, sucrose, dextrose, and natural gums.

Conventional starch binders such as pregelatinized, modified and stabilized waxy maize starch, pregelatinized corn starch, pregelatinized tapioca or potato starch, stable modified amylopectin, low viscosity tapioca dextrin, dextrinized corn starch and/or cold-water-swelling pregelatinized corn starch, which are water-soluble and have limited, if any, direct compression properties, typically are not used in direct compression tabletting, but are suitable for wet granulation. Such wet granulation binders may be used in a blend wherein another binder(s) provides direct compressibility. Such blends are useful in hybrid wet granulation-direct compression tabletting processes.

Typical direct compression binders include microcrystalline cellulose, compressible sugars, specific calcium salts, lactose, and dextrose. Of these, microcrystalline cellulose is the preferred binder and it also displays good disintegration properties. However, tablets made with this binder tend to have dull rough surfaces. Also microcrystalline cellulose is very expensive. Other preferred binders include the calcium phosphates (di- or tribasic) and compressible sugars, but each has its disadvantage. Namely, the calcium salts do not allow one to prepare tablets with a high level of active ingredient and generally require the use of disintegrants. The sugars (mostly made up of sucrose) present a darkening problem, tend to increase in hardness with age, and may react with drugs. Lactose has limited binding properties and exhibits a browning reaction when exposed to heat and moisture; it also requires the use of a disintegrant. Mannitol and sorbitol have certain taste advantages but either lack binding properties and require a disintegrant or are too hygroscopic or too expensive.

Physically modified, partially cold-water-swelling, cold-water-soluble compacted starches are reportedly useful as binder-disintegrants for direct compression tabletting (see U.S. Pat. Nos. 3,622,677 and 4,072,535 issued Nov. 23, 1971 and Feb. 7, 1978 to R. W. Short, et al.) and as free-flowing fillers for dry dosage capsules (see U.S. Pat. No. 4,072,535 cited above). The modification, which is carried out by passing the starch through closely spaced steel rollers with or without the use of supplemental thermal energy, disrupts and fractures at least some of the granules and results in a mixture of birefringent and non-birefringent granules and fragments, as well as completely solubilized starch (typically about 10–20%). The compacted mass is ground and classified into particle size fractions. The resulting starch does have limited direct compression binding but the loading potential is low and the use of an auxiliary binder is often required.

Hydrolyzed starches, such as dextrinized starches having a dextrose equivalent of from about 0.5–50, are used as "melting point elevators" in a hybrid wet granulation-direct compression tabletting process for preparing nonfriable, rapidly water-soluble tablets such as sweetened or unsweetened beverage tablets (see U.S. Pat. No. 4,384,005 issued May 17, 1983 to D. R. McSweeney). An aqueous moistener comprising corn syrup and optionally glycerine is added to the dry mix containing the acidulant and optional components, and the hydrolyzed starch is added in an amount sufficient to function as a melting point elevator and also to convert the moistened mixture into a free-flowing mixture suitable for direct compression. The melting point elevator raises the melting point of the mixture so that the tablet will not soften, melt or form a hard core during the optional drying step that follows tablet formation.

Starch fractions, such as non-granular amylose, are also reportedly useful as binder-disintegrants in direct compression or double compression (dry slugging) tabletting processes (see U.S. Pat No. 3,490,742 issued Jan. 20, 1970 to G. K. Nichols, et al.). The amylose fraction is non-granular because the starch from which it is derived is totally solubilized in order to free the amylose. This material is prepared by gelatinizing the starch and then fractionating high molecular weight (long chain) amylose from the gelatinized starch in water at elevated temperatures. The binder-disintegrant must contain at least 50% of the native (e.g., long chain) amylose which was present in the starch.

U.S. Pat. No. 4,551,177, issued Nov. 5, 1985 to Trubiano, et al. discloses compressible starch, useful as a binder for tablets prepared by direct compression or dry granulation or as a binder-diluent for capsules, which consists essentially of a free-flowing compressible starch powder derived from a cold-water-insoluble, granular starch by treatment with an acid, alkali, and/or alpha-amylase enzyme at a temperature below the gelatinization temperature of the starch, the treated starch being characterized by altered, weakened granules with a less dense interior and disrupted surface, the starch powder effectively binding when compressed.

None of these starch products display all of the desirable binder properties of microcrystalline cellulose in direct compression tabletting. Due to the high cost of microcrystalline cellulose, there is a need for compressible starches which are suitable for use as binders in any tabletting method, especially direct compression, and which are likewise useful as binder-diluents for capsule filling operations. Additionally, a glossy smooth surface is frequently a desirable attribute in tablets and there is a need for a binder which creates such a surface appearance.

It has been found that starch containing greater than about 90% amylopectin, which starch has been highly or partially enzymatically debranched by treatment with an alpha-1,6-D-glucanohydrolase, such as pullulanase or isoamylase, to yield a starch hydrolysate comprising at least 20%, by weight, short chain amylose, is an excellent direct compression tablet binder which provides a glossy, smooth surface to tablets. Additionally, the debranched starch may be selected such that its functional properties are suited for a variety of tablet excipient functions.

SUMMARY OF THE INVENTION

A tablet excipient, and, in particular, a tablet binder, comprising a starch containing greater than about 90% amylopectin, which starch has been enzymatically treated with an alpha-1,6-D-glucanohydrolase, such as pullulanase or isoamylase, to debranch the starch and yield at least 20%, by weight, short chain amylose, is provided herein. Also provided herein is a process for preparing highly crystalline short chain amylose from the debranched starch. The debranched starch may also comprise amylopectin, partially debranched amylopectin, or combinations thereof and will be substantially free of long chain amylose. These tablet excipients are useful in direct compression tabletting and other tabletting operations.

As used herein "tablet" includes tablets, capsules, pellets, granules, and the like, which employ excipients to deliver active agent(s). "Excipient" includes binders and all other excipients described herein.

As used herein, the term "short chain amylose" refers to linear polymers containing from about 5 to 65 anhydroglucose units linked by alpha-1,4-D-glucoside bonds. "Long chain amylose" refers to that natively occurring linear fraction of starch which generally comprises in excess of 250 anhydroglucose units.

Fully debranched starch theoretically comprises 100%, by weight, of short chain amylose; in practice, depending upon the type of starch employed the product may be highly debranched such that further enzyme activity produces no measurable change in the percentage of short chain amylose. The starch may be modified by derivatization, crosslinking or conversion.

DESCRIPTION OF THE PREFERRED EMBODIMENTS

Starches suitable herein include any starch containing greater than about 90% amylopectin, the starch being susceptible to attack by a debranching enzyme, such as pullulanase, with the resultant hydrolysis of the alpha-1,6-D-glucosidic bond. Any waxy-type starch may be employed. Suitable starches include waxy maize, waxy rice, waxy barley, waxy sorghum as well as the waxy hybrids of tapioca, wheat, potato and the like.

The starch is pregelatinized to permit efficient and uniform enzymatic debranching. It may be used in a dried form or as an aqueous dispersion following gelatinization. Numerous methods of pregelatinizing starch, such as direct and indirect heating by jet-cooking, drum-drying, spray-drying and steam injection atomization processes, as well as chemical (e.g., NaOH) or mechanical (e.g., extrusion) gelatinization processes, are well known in the art. Any method may be used herein. In a preferred embodiment, the starch is slurried in water and jet cooked at approximately 300° F. (149° C.) to instantaneously gelatinize the starch.

Converted starches may be used herein. Conversion degrades the starch and reduces the viscosity of the cooked starch dispersions. Suitable conversion of the starches to thin-boiling or fluidity starches useful herein may be achieved by standard oxidative, heat, acid or alpha-amylase enzyme conversion techniques which are well known in the art. A method for starch conversion employing alpha-amylase enzyme is disclosed in U.S. Pat. No. 4,726,957 to Lacourse, et al., and is well known in the art.

Dextrinized starches may also be employed herein.

It will be appreciated by the practitioner that, while acid-, oxidative- and enzyme-conversions may be carried out on either a derivatized starch or an underivatized starch, it is common practice to use the underivatized starch for the acid- or oxidative- conversions and for dextrinizations.

Derivatized starches and starches that have been converted and derivatized are suitable for debranching and for use as tablet binders. Suitable derivatives include esters such as the acetate and half-esters such as the succinate and octenylsuccinate prepared by reaction with acetic anhydride, succinic anhydride and octenylsuccinic anhydride ("OSA"), respectively; the phosphate derivative prepared by reaction with sodium or potassium orthophosphate or tripolyphosphate; ethers such as hydroxypropyl ether prepared by reaction with propylene oxide; and any other suitable starch derivatives. Those approved for use in food products and/or drugs are preferred.

Each modified starch should have a suitable degree of substitution (D.S.) and/or conversion to provide a balance between properties related to fat-binding, flowability, thermal stability, molecular size, and the like, and compression characteristics as desired by the practitioner. The amounts of derivatizing reagent used will depend upon the type of reagent, the amylopectin content of the starch or starch mixtures, and the amount of conversion and debranching. Typically, as the conversion, crosslinking or derivatization is increased, the debranching should be controlled to provide a proper balance of properties and maintain compressibility. The practitioner will also recognize that the compression characteristics required will vary with the compressibility of the active ingredient, the load of the ingredient in the tablet, other ingredients in the tablet, and the method of manufacture of the tablet.

The OSA starch derivatives are preferred when better emulsifying or fat-binding properties are required. The practitioner will recognize that the emulsifying properties required will depend not only on the oil or fat content of the tablet but also on the tablet's intended use (e.g., bouillon cube). The preferred starch derivatives for fat-binding or emulsifying formulations are jet-cooked, debranched starch derivatives which have been prepared by treatment with up to 3% octenylsuccinic anhydride, or jet-cooked, acid-converted debranched OSA starch derivatives having a water fluidity of 85 or less.

The starches may be derivatized or crosslinked before or after debranching to provide heat and shear tolerance in the manufacture, use or storage of the tablet.

Crosslinked starches useful herein may be prepared according to procedures described in the prior art. The reaction conditions employed will vary with the type of crosslinking agent used, as well as the type of starch, the batch size, and the like.

Crosslinking agents suitable for food and pharmaceutical starches include epichlorohydrin, phosphorous oxychloride, sodium trimetaphosphate, and adipic-acetic anhydride. Treatments with sodium trimetaphosphate providing up to 0.4% residual phosphate, calculated as phosphorus, are permitted for food use. Treatments with adipic-acetic anhydride may include up to 0.12% adipic anhydride and may provide a maximum of about 2.5% bound acetyl. Phosphorus oxychloride is preferred at treatment levels of about 0.1%, by weight of starch. The starch also may be derivatized by treatment with up to about 25% propylene oxide or up to about 4% succinic anhydride to yield the corresponding starch derivative. These treatment levels, and the OSA treatment levels, are preferred because they fall within the Food and Drug Administration's regulatory limits. Other treatment levels may be preferred for non-foods.

The above starch modification procedures, i.e., pregelatinization, conversion, dextrinization, derivatization, and crosslinking are conventional, well-known to those skilled in the art, and described in such publications as "Starch and Its Modifications" by M. W. Rutenberg, pp. 22–36, in *Handbook of Water-soluble Gums and Resins*, Robert L. Davidson (Editor), McGraw Hill Book Co., New York, N.Y., 1980.

In the preparation of the modified starches, the conversion or dextrinization, is typically carried out prior to the pregelatinization step. It is possible, however, to pregelatinize the starch prior to these treatments. Likewise, the derivatization or crosslinking is typically carried out prior to pregelatinization; however, this sequence can also be reversed. Debranching may be carried out on modified (i.e., derivatized, crosslinked, dextrinized or converted) or unmodified starch but pregelatinization must be carried out before the debranching process to insure a uniform product.

In a preferred embodiment, the next step after preparing the modified starch is to gelatinize the starch, thereby disrupting, in whole or in part, the associative bonding of the starch molecules in the granular structure, making the molecule more accessible to the enzyme, and permitting the enzyme to more easily and uniformly debranch the starch molecules. After the starch has been gelatinized, the solids, temperature and pH of the aqueous starch dispersion are adjusted to provide maximum enzyme activity.

Optimum parameters for enzyme activity will vary depending upon the enzyme used. Thus, the rate of enzyme degradation depends on factors including enzyme concentration, substrate concentration, pH, temperature, the presence or absence of inhibitors and other factors. Depending on the type of enzyme, or its source, various parameters may require adjustment to achieve optimum digestion rate. In general, the preferred enzyme digestion reaction is carried out at the highest feasible solids content to facilitate subsequent drying of the starch composition while maintaining optimum reaction rates. For example, for the pullulanase used herein to produce a starch suitable for use as a tablet binder, a precooked starch dispersion ranging up to 28% solids is preferred.

The practitioner will recognize that a higher solids starch system (e.g., above 50% solids) may be employed if the starch is gelatinized in a process which produces adequate mixing to uniformly blend the enzyme with the starch at higher solids. The practitioner will also recognize that the temperature, treatment time and other parameters of the enzymatic debranching process must be adjusted to the higher solids content. Processes which employ higher solids dispersions are intended to fall within the scope of this invention and may be used to prepare the debranched starch herein.

Although the process of this invention is illustrated employing pullulanase (E.C. 3.2. 1.41, pullulan 6-glucanohydrolase) as the enzyme component, other endo-alpha-1, 6-D-glucanohydrolases such as isoamylase (E.C. 3.2. 1.68), or any other endo-enzyme which exhibits selectivity in cleaving the 1,6-linkages of the starch molecules, leaving the 1,4-linkages substantially intact, and yielding short chain amylose, may be used to prepare the debranched starch herein.

In a preferred embodiment, the enzyme used is a heat stable debranching enzyme obtained from a novel species of Bacillus. It belongs to the group of debranching enzymes known as pullulanases. It catalyzes the hydrolysis of the alpha-1,6 linkages in pullulan and amylopectin, provided that there are at least two glucose units in the side chain. Pullulan is a linear polymer consisting essentially of D-glucopyranosyl triose units joined by alpha-1,6 linkages.

Optimum concentrations of enzyme and the starch substrate are governed by the level of enzyme activity and the enzyme source.

Although the process of this invention makes use of an enzyme in solution, processes utilizing an enzyme immobilized on a solid support are intended to fall within the scope of this invention.

The debranching may proceed in the presence of buffers to ensure that the pH will be at the optimum level throughout the degradation. Buffers such as acetates, citrates, or the salts of other weak acids are acceptable. Other agents may be used to optimize enzyme activity. The reaction may be carried out in a pH range from about 3 to 7.5, with the preferred range being between 4.5 and 5.5 and the optimum being 5.0 at 60° C. for the *Bacillus pullulanase*.

The aqueous starch dispersion should be held during the enzymatic debranching at a temperature of about 25°–100° C., the preferred range being 55°–65° C. and the optimum being 60° C. at pH 5.0 for the *Bacillus pullulanase*. However, if shorter treatment times are desired, a temperature range from 60°–65° C. or a higher enzyme concentration may be used. Alternatively, higher temperatures may be employed if a thermally stable debranching enzyme which yields short chain amylose from starch is selected for use herein. As with other parameters which define enzymatic activity, the preferred and optimum temperature ranges will vary with changes in other parameters such as substrate concentration, pH and other factors, and can be determined by the practitioner.

The enzyme reaction is permitted to continue until the desired level of debranching is reached. The progress of enzyme reaction may be measured by various methods. If all critical parameters have been established for achieving a particular starch composition, then the reaction may be allowed to proceed to a predetermined relative end point in time. The end point also may be monitored and defined by measuring the concentration of reducing groups which are freed by alpha-1,6-D-glucanohydrolase activity by methods well known in the art. Other techniques such as monitoring the change in viscosity, iodine reaction, or the change in molecular weight may be used to define the reaction end point. When the starch is highly debranched, the short chain amylose will precipitate out of the debranched starch dispersion upon standing (at the preferred starch solids range, e.g., 28%) and the end point is reached when no further precipitate is formed. The precipitate may be re-suspended and the dispersion may be spray-dried, preferably at a temperature in excess of 60° C., to yield a product containing at least 70%, by weight, short chain amylose. In addition, the short chain amylose may be recovered by filtering and washing the precipitate and spray-drying the washed precipitate, preferably at a temperature in excess of 60° C.

The short chain amylose content is preferably measured by gel permeation chromatography. After separating the starch into its different molecular weight fractions by gel permeation chromatography, the percentage of short chain amylose is determined by calculating the percentage, by weight, of the partially debranched starch which is eluted in the low molecular weight fraction. It will be understood by the practitioner that these percentages are approximately equal to the amount of short chain amylose which has been liberated from the amylopectin by the debranching enzyme. Experimental error in gel permeation chromatography (e.g., due to contamination by the enzyme, or by sugars or dextrins introduced with the starch, the enzyme solution, the buffer or other process components) may result in a low molecular weight fraction (oliogosaccharides) which may range up to about 5% more than the percent short chain amylose in the starch sample. In the case of samples which are washed or otherwise purified, this soluble low molecular weight fraction of the oliogosaccharides will be removed leading to more highly crystalline short chain amylose portions.

The degree of starch debranching needed for tabletting applications depends on the function of the starch in the tablet, the type of starch utilized, the degree, if any, of conversion, derivatization, crosslinking or dextrinization and the type and amount of active ingredient, the tablet formulation, the physical form (capsule, pellet, granule, tablet), and other requirements of tablet manufacture.

Useful starches include waxy maize, waxy rice, waxy barley, waxy sorghum and waxy hybrids such as those of tapioca, potato and the like. In a preferred embodiment, the starch is highly debranched to yield large portions of highly crystalline, short chain amylose. Typically, starches containing large percentages of amylopectin yield about 75 to 90% short chain amylose. Partially debranched starches, containing from about 20 to 75% short chain amylose, are also preferred for use herein.

After the desired degree of starch debranching has been reached, the enzyme may be deactivated. Pullulanase is rapidly deactivated at temperatures above about 70° C., therefore, the reaction may be conveniently terminated by increasing the temperature of the starch dispersion to at least 75° C. for about 15 minutes. If the starch is highly debranched, it may not be necessary to deactivate the enzyme. The debranched starch may be recovered by separating the short chain amylose crystalline precipitate from the mother liquor (containing soluble starch fragments, the enzyme and other reaction by products) and dewatering the short chain amylose. Derivatization and other modifications of the debranched starch may be carried out after debranching is complete.

If purification of the debranched starch composition is required, reaction impurities and by-products may be removed by dialysis, filtration, centrifugation or any other method known in the art for isolating and concentrating starch compositions. The highly debranched starch may be dewatered by centrifugation, filtration and other methods known in the art.

If a dried starch composition is desired, the starch may be dried by spray-drying, flash-drying, or any drying method known in the art.

The debranched starches may be employed in blends which are useful as tablet binders. For example, starch binders useful in wet granulation typically have some water-soluble or water-dispersable qualities and are limited in their direct compressibilty. Such starches are used in the wet granulation stage of a hybrid tablet manufacturing process. Typically, this stage is followed by a dry stage wherein the wet granules (bound by the water soluble starch binder) are compressed into a dry final tablet. The debranched starches are useful as a direct compression binder in the dry stage. Thus, a blend of the two types of starches is useful in these formulations. The wet granulation binders useful in the binder admixture are conventional, well-known and discussed previously. Pregelatinized starches such as corn starch are preferred herein.

A variety of starch compatible active agents may be employed in the tablets of this invention. The particular nature of the active ingredient is not critical, and pharmaceutical and non-pharmaceutical active ingredients, such as pulverized detergents, dyes, pesticides, agricultural chemicals, enzymes, and foods may be employed. Typical products include pills, drug and vitamin capsules and tablets, fertilizers, pesticides, rodenticides, animal feed pellets, charcoal briquets, bouillon cubes and other seasoning tablets and the like. The word "tablet" is used herein in its broadest sense and is meant to include all such products.

When necessary, disintegrants may be used and these include native starches, modified starches, gums, cellulose derivatives, microcrystalline cellulose, clays, effervescent mixtures, and enzymes.

The amount of binder (or binder admixture), active ingredient, and lubricant, disintegrant and/or diluent, if any, will depend not only on potency desired but also on the compatibility of the components, the tabletting method used, the amount of debranching and the percent short chain amylose, and also the hardness, friability, disintegrability, dissolution, and/or stability of the final tablet. The amount of binder-diluent used in the dry dosage capsules will likewise depend on various factors. Given the minimum and preferred characteristics desired in the final product, the tolerable limits on the weight ratio of the components may be easily determined by the skilled practitioner. Anti-adhesives, glidants, flavors, coloring agents, and the like may also be used. They are incorporated in appropriately effective amounts into the tablets herein.

As may be readily determined by the practitioner, particular embodiments of the debranched starches disclosed herein may be selected as tablet excipients which function as binder(s), moisture absorbent(s) (e.g., starch dried to 2–3% moisture), binder-disintegrant(s), filler(s) or diluent(s), glident(s), lubricant(s), or flow agent(s), tablet surface gloss or hardness agent(s), or a combination thereof.

The following examples will more fully illustrate the embodiments of this invention. In the examples, all parts are given by weight and are based on the weight of the starch, and all temperatures are in degrees Celsius.

The following procedures were used to characterize the debranched starches useful herein, to monitor their preparation, and to prepare and evaluate tablets containing these compressible starches.

WATER FLUIDITY MEASUREMENT

The water fluidity of the starches is measured using a Thomas Rotational Shear-Type Viscometer (manufactured by Arthur H. Thomas Co., Philadelphia, Pa. 19106), standardized at 30° C. with a standard oil having a viscosity of 24.73 cps., which oil requires 23.12±0.05 sec. for 100 revolutions. Accurate and reproducible measurements of the water fluidity are obtained by determining the time which elapses for 100 revolutions at different solids levels depending on the starch's degree of conversion (as conversion increases, the Water Fluidity increases and the viscosity decreases). The procedure used involves slurrying the required amount of starch (e.g., 6.16 g, dry basis) in 100 ml of distilled water in a covered copper cup and heating the slurry in a boiling water bath for 30 minutes with occasional stirring. The starch dispersion is then brought to the final weight (e.g., 107 g) with distilled water. The time required for 100 revolutions of the resultant dispersion at 81°–83° C. is recorded and converted to a water fluidity number using a conversion table.

| Time Required for 100 Revolutions (seconds) | | | | Water |
|---|---|---|---|---|
| Amount of Starch Used (anhydrous, g): | | | | |
| 6.16[a] | 8.80[b] | 11.44[c] | 13.20[d] | Fluidity |
| 60.0 | | | | 5 |
| 39.6 | | | | 10 |
| 29.3 | | | | 15 |
| 22.6 | | | | 20 |
| 20.2 | | | | 25 |

-continued

| Time Required for 100 Revolutions (seconds) | | | | Water |
|---|---|---|---|---|
| Amount of Starch Used (anhydrous, g): | | | | |
| 6.16[a] | 8.80[b] | 11.44[c] | 13.20[d] | Fluidity |
| | 33.4 | | | 30 |
| | 27.4 | | | 35 |
| | 22.5 | | | 40 |
| | | 32.5 | | 45 |
| | | 26.8 | | 50 |
| | | 22.0 | | 55 |
| | | | 24.2 | 60 |
| | | | 19.2 | 65 |
| | | | 15.9 | 70 |
| | | | 13.5 | 75 |
| | | | 11.5 | 80 |
| | | | 10.0 | 85 |
| | | | 9.0 | 90 |

For [a], [b], [c], and [d], final weights of starch solutions are 107, 110, 113, and 115 g, respectively.

GEL PERMEATION CHROMATOGRAPHY

Starches were prepared for analysis by slurrying 5 mg of starch in 4 ml of dimethylsulfoxide ("DMSO") containing 0.3M sodium nitrate and heating the slurry to 80° C. for at least 30 minutes. Samples (200 ul) were injected into an ALC/GPC-150C Chromatograph (Waters Associates, Milford, Mass.) (equipped with a Nelson 3000 Series Chromatography Data System and two PLgel mixed 10 um columns (Polymer Laboratory, Amherst, Mass.), employing DMSO containing 0.03M sodium nitrate as the mobile phase), and eluted at a rate of 1 ml/min. The columns were calibrated using dextran standards (with molecular weights of 2,000; 20,000; 80,000; 500,000; and 2,000,000, obtained from Pharmacia Fine Chemicals, Piscataway, N.J.). The percentage short chain amylose was calculated from the relative area of the peak obtained within the molecular weight range from about 500 to 20,000.

EXAMPLE 1

This example illustrates the preparation of the debranched starches and tablets containing these starches.

PREPARATION OF THE DEBRANCHED STARCH

The starches were converted, crosslinked, derivatized or dextrinized, where applicable, prior to gelatinization and treatment with pullulanase. To convert the starch, a slurry of 100 parts in 150 parts of water was heated to 52° C., the indicated amount of hydrochloric acid (1.75%) was added, and the mixture was stirred for 16 hours at 52° C. The hydrolysis was stopped by neutralizing the mixture with alkali (a solution of 3% sodium hydroxide) to a pH of 5.5. The converted starch was recovered by filtration, washed and dried.

To prepare the octenylsuccinate derivative, 100 parts of starch was slurried in 150 parts water, the pH was adjusted to 7.5 with sodium hydroxide, and the indicated amount of octenylsuccinic anhydride was added slowly while the pH was maintained at 7.5 with the alkali. The reaction was complete when no further addition of alkali was necessary. The pH was adjusted to between 4.0 and 6.5 and the resulting derivatives were recovered by filtration, washed and dried.

To prepare the acetate derivative, 100 parts of the starch was slurried in 150 parts water, adjusting the pH to 8.0 with 3% sodium hydroxide solution, and slowly adding the indicated amount of acetic anhydride while maintaining the pH at 8.0 with the above alkali. The reaction was complete when no further addition of alkali was necessary. The pH was adjusted to between 4.0 and 6.5 and the resulting derivative was recovered as above.

The crosslinked starch was prepared by slurrying 100 parts of starch in 150 parts water, adding 0.8 part sodium hydroxide, 1.0 part sodium chloride, and then adding the indicated amount of phosphorus oxychloride. The slurry was agitated for 3 hours at room temperature. When the reaction was completed, the pH was adjusted to 5.5 with acid. The starch was recovered by filtration, washed, and dried.

An aqueous slurry (20–30% solids) was prepared employing one of these modified starches, or where applicable, a native starch. The aqueous starch slurry was jet cooked at approximately 300° F. (149° C.) to gelatinize the starch. The cooked starch dispersion was placed in a constant temperature bath at 58°–60° C. with constant stirring. The pH was adjusted to 5 with 3% hydrochloric acid.

Depending on the type of starch used and its amylopectin content, between 0.5 and 10.0 mls of pullulanase per 100 g of starch were added to the cooked starch dispersion. The pullulanase (E.C. 3.2.1 41, pullulan 6-glucanohydrolase) which was used is a starch debranching enzyme produced by a novel species of Bacillus. This enzyme (Promozyme™) was obtained from Novo Industri A/S of Denmark. The enzymatic activity of a 1.25 g/ml solution of Promozyme is standardized at 200 PUN/ml of solution. One PUN (Pullulanase Unit Novo) is the amount of enzyme which, under standard conditions, hydrolyzes pullulan, liberating reducing carbohydrate with a reducing power equivalent to 1 micro-mol glucose per minute. The procedure for determining PUN is available from Novo Industri A/S. Thus, for example, for a waxy maize starch dispersion (with higher amylopectin content), 750 PUN of pullulanase per 100 g waxy maize starch were added to the dispersion.

The pullulanase was permitted to debranch the starch until the desired short chain amylose content had been reached, or until the starch had been highly debranched. The highly debranched starch formed a highly crystalline precipitate upon standing which was filtered and washed before spray-drying, as described below, or flash-drying, at an inlet temperature of 71°–110° C. and an outlet temperature of 50°–85° C. The pullulanase was deactivated in preparing partially debranched starch by heating the dispersion to at least 80° C. The starch dispersion was spray dried at an inlet temperature of 200°–210° C. and an outlet temperature of 120°–125° C. The spray dried starch was screened through #40 mesh screen.

PREPARATION OF HIGHLY CRYSTALLINE SHORT CHAIN AMYLOSE

A 28% solids slurry of waxy maize starch in water was jet cooked at 149° C. (300° F.) to yield a 25% solids starch dispersion. The dispersion was placed into a constant temperature water bath at 60° C., the pH was adjusted to 5.0 and 8 mls of the Promozyme pullulanase/100 g starch were added to the dispersion. The enzyme reaction was permitted to continue with continuous stirring for 88 hours.

Upon standing, a highly crystalline precipitate was formed in the milky starch dispersion.

This precipitate was filtered, washed three times and air-dried to yield a highly crystalline short chain amylose in about 85% yield. Gel permeation chromatography indicated the product contained 84% short chain amylose.

A second dispersion of waxy maize starch was debranched in the same manner except that the enzyme reaction was continued for 48 hours and filtering and washing steps were omitted. Thereafter the dispersion was spray-dried at 26% solids in a Niro laboratory spray-drier at an inlet temperature of 210° C. and an outlet temperature of 125° C. The product, which comprised 78% short chain amylose, was recovered in about 75% yield. Although this product was highly debranched, in the absence of the purification step, it was not highly crystalline.

PREPARATION OF TABLETS

Direct compression tabletting in a laboratory scale tablet press (Stokes, Model B-2, 16 station rotary tablet press with ⅜" standard concave punches, obtained from Stokes Co., Warminster, Pa.) was used to prepare tablets from the following formula:

| Ingredient | Formula Percentage, by weight | Function |
|---|---|---|
| Acetaminophen (APAP)[a] | 64.00 | Active Ingredient |
| Binder | 34.75 | Binder |
| Magnesium Stearate[b] | 1.00 | Lubricant |
| Amorphous Fumed Silica[c] | 0.25 | Flow Agent |

[a]USP powder, obtained from Mallinckrodt, St.Louis, Missouri.
[b]NF powder, obtained from Ruger Chemical Co., Irvington, New Jersey.
[c]Cab-O-Sil ®, obtained from Cabot Corporation, Tuscola, Illinois.

All ingredients except the binder were dry blended, screened through a 10 mesh sieve and blended with the binder.

Tablets weighing from 360–460 mg were formed in the tablet press at pressure settings from A (low) to I (high) by adjusting the weight setting for each pressure setting. Compressibility is expressed as a profile obtained by increasing the pressure setting until the accompanying increases in the tablet hardness measurements leveled off. Tablet hardness was determined on a hydraulic tablet hardness tester (Delamar, Model PT 1000, obtained from VanKel Industries, Edison, N.J.)in units of Kg/cm².

The active ingredient, acetaminophen (APAP), does not compress to form a tablet in the absence of a binder even under extreme pressure. Thus, binders effective in a formula containing acetaminophen (particularly in the very high load tablet formula employed herein) would be effective in substantially all commercial tablet formulations.

Example 2

This example illustrates that the highly debranched starches of this invention are excellent binders which compare very favorably to commercially used binders in direct compression tabletting.

The starch debranching and tabletting methods of Example 1 were employed to make direct compression tablets according to the formula of Example 1. The commercial binders used as controls are listed in Tables I and II, below. Compression profiles and visual observations of structurally weak, capped or split tablets are set forth in Tables I and II.

TABLE I

BINDER PROFILE
Direct Compression APAP Formula

| MA-CHINE POSITION | 100%[a] APAP | Waxy[b] Maize Starch | Corn[b] Starch | Potato[b] Starch | Isolated[c] Potato Amylose | Modified[d] Starch | Modified[e] Starch |
|---|---|---|---|---|---|---|---|
| A | 0 |     |     |     |     |     |     |
| B | 0 | 2.0 | 2.1 | 1.3 |     |     |     |
| C | 0 | 3.0 | 2.5 | 2.5 |     |     | 1.2 |
| D | 0 | 3.1 | 3.1 | 2.3 |     |     | 2.4 |
| E | 0 | 3.4 | 2.7 | 2.0 | 1.0 | 1.0 | 3.9 |
| F | 0 | 3.3 | 2.0 | 2.0 | 1.0 | 1.0 | 3.0 |
| G | 0 | 3.0 |     | 1.8 |     | 1.3 | 3.3 |
| H | 0 |     |     | 1.5 |     | 2.5 | 2.9 |
| I | 0 |     |     |     |     | 2.0 | 2.4 |

[a]Not compressible.
[b]Poorly compressible; structurally weak, capped, split tablets.
[c]Poorly compressible; structurally weak, capped, split tablets. Modified starch binder made by the method of U.S. Pat. No. 3,490,742.
[d]Poorly compressible; structurally weak, capped, split tablets. Modified starch binder made by the method of U.S. Pat. No. 4,072,535 ("Starch 1500," obtained from Colorcon, Inc., West Point, PA).
[e]Modified starch binder made by the method of U.S. Pat. No. 4,551,177. Tablets were structurally intact when removed from the tablet press.

TABLE II

BINDER PROFILE
Direct Compression APAP Formula

| MA-CHINE POSITION | Hydrous[a] Lactose | Calcium[a] Phosphate | Microcrystalline Cellulose[b] | Debranched Starch[c] | Debranched Starch[d] | Debranched Starch[e] |
|---|---|---|---|---|---|---|
| A |     |     | 1.6 | 1.5 | 3.3 | 3.8 |
| B |     |     | 2.8 | 2.6 | 4.8 | 6.1 |
| C |     |     | 4.2 | 3.5 | 6.1 | 10.1 |
| D |     |     | 5.4 | 4.7 | 7.0 | 10.4 |
| E | 1.0 | 1.0 | 6.3 | 7.2 | 7.2 | 10.2 |
| F | 1.0 | 1.0 | 5.6 | 7.8 | 6.0 | 10.4 |
| G |     |     | 5.4 | 7.6 | 5.3 | 10.0 |
| H |     |     | 5.5 | 6.6 | 4.1 | 9.5 |
| I |     |     |     |     |     | 9.3 |

[a]Poorly compressible; structurally weak, capped, split tablets. Fast Flo #316, hydrous lactose obtained from Foremost Whey Products, Baraboo, Wisconsin; Emcompress, dibasic calcium phosphate dihydrate, obtained from Edward Mendell Co., Carmel, New York.
[b]Avicel pH 101, microcrystalline cellulose, obtained from FMC Corporation, Newark, Delaware.
[c]Highly debranched waxy maize starch (77.0% short chain amylose) prepared by the method of Example 1.
[d]Highly debranched waxy maize starch (84.3% short chain amylose) prepared by the method of Example 1.
[e]Highly debranched waxy maize starch (85.2% highly crystalline short chain amylose) prepared by the method of Example 1.

The results show that native starches (waxy maize, corn and potato) form structurally weak tablets, most of which split or show capping (a split which leaves the top (cap) portion of the tablet in the mold). Although the compressibility (weight vs. hardness) profile shows some binding capacity, the failure of tablet integrity makes native starches unacceptable as binders, particularly in a high load (64%) APAP formulation. Similar results were obtained with isolated potato amylose (U.S. Pat. No. 3,490,742) and starch modified by the method of U.S. Pat. No. 4,072,535.

Some binding capacity was observed in the compressibility profiles of 1) modified starch prepared by the method of U.S. Pat. No. 4,551,177; 2) hydrous lactose; and 3) dibasic calcium phosphate dihydrate. However, only the modified starch of U.S. Pat. No. 4,551,177 formed tablets which remained intact upon removal from the press, did not split and did not show capping. The lactose- and calcium phosphate-containing tablets were structurally weak, capped and split. The best compressibility and structural integrity was observed in the tablets prepared from microcrystalline cellulose and highly debranched waxy maize starches (77.0–85.2% short chain amylose). The debranched starches were superior in compressibility, especially the highly crystalline version. Additionally, the tablets made from debranched starch had a smooth glossy surface and remained intact after they were removed from the tablet press.

EXAMPLE 3

This example illustrates that partially debranched starches (containing from about 20 to 60% short chain amylose) are effective tablet binders.

The formula and methods of Example 1 were employed to test the partically debranched starches listed in Table 3, below. Results are set forth in Table III.

TABLE III

BINDER PROFILE
Direct Compression APAP Formula

| MA-CHINE POSITION | Tablet Hardness in Kg/cm² for Partially Debranched Starches | | | | |
|---|---|---|---|---|---|
| | 24.5% SCA* | 28.0% SCA* | 32.6% SCA* | 52.4% SCA* | 60.1% SCA* |
| A | | | | | |
| B | 2.0 | | 2.5 | 2.5 | |
| C | 2.0 | | 2.0 | 3.0 | |
| D | 2.0 | | 2.5 | 3.0 | |
| E | 2.0 | 3.3 | 2.5 | 3.3 | 2.5 |
| F | 3.0 | 3.0 | 3.0 | 3.0 | 2.8 |
| G | 2.0 | 3.0 | 2.5 | 2.8 | 3.3 |
| H | 2.0 | 3.3 | 2.0 | 2.5 | 5.3 |
| I | 1.5 | 2.0 | 2.0 | 2.0 | 2.0 |

*Short chain amylose content of the partially debranched waxy maize starch.

The results show tablet binder performance similar to that of the commercially used binder, the modified starch of U.S. Pat. No. 4,551,177, and better than that of lactose and calcium phosphate binders (see Tables I and II), in that the tablets were compressible (but less compressible than microcrystalline cellulose) and retained their structural integrity upon removal from the press. The partially debranched starches also formed tablets with a smooth glossy surface.

One skilled in the art will recognize that test conditions (e.g., the high load APAP formula) employed in these examples are more rigorous than those encountered in commercial operations. Thus, the superior performance of debranched starches under such conditions indicates that these starches are useful in substantially all tabletting operations requiring a binder with direct compressibility.

Now that the preferred embodiments of the present invention have been described in detail, various modifications and improvements thereon will become readily apparent to those skilled in the art. Accordingly, the scope and spirit of the invention are to be limited only by the claims and not by the foregoing specification.

We claim:

1. A process for preparing a tablet, comprising the steps:
   a. enzymatically treating a starch containing greater than 90% amylopectin with an alpha-1,6-D-glucanohydrolase to debranch the starch and yield at least 20%, by weight, of a short chain amylose of from about 5 to 65 anhydroglucose units linked by alpha-1,4-D-glucoside bonds;
   b. drying the starch;
   c. blending the starch with at last one active agent to form a blend; and
   d. compressing the blend to form a tablet;
   wherein the starch is characterized by sufficient compressibility for use as an excipient, a binder, a binder-disintegrant, a binder-diluent, filler or diluent, a moisture absorbent, a glidant, lubricant or flow agent, a surface gloss or hardness agent, or a combination thereof, in the tablet.

2. The process of claim 1, wherein the starch is waxy maize, waxy rice, waxy barley, waxy sorghum or waxy hybrids of potato, tapioca or wheat.

3. The process of claim 1 further comprising the step of modifying the starch by derivatization, conversion, crosslinking or dextrinization either before or after the debranching step.

4. The process of claim 3, wherein the starch is derivatized by treatment with up to about 25% propylene oxide, or up to about 4% succinic anhydride, or up to about 3% octenyl succinic anhydride, or a sufficient amount of acetic anhydride to provide a maximum of about 2.5% bound acetyl, or a sufficient amount of sodium or potassium orthophosphate, sodium or potassium tripolyphosphate, or mixture thereof to provide a maximum of about 0.4% residual phosphate.

5. The process of claim 3, wherein the starch is crosslinked by treatment with phosphorous oxychloride, epichlorohydrin, sodium trimetaphosphate, or adipic-acetic anhydride.

6. The process of claim 3, wherein the starch is converted to a water fluidity of up to 85 by acid or enzyme-conversion, or by oxidation.

7. The process of claim 1, wherein the starch is enzymatically treated with a debranching enzyme selected from the group consisting essentially of pullulanase and isoamylase.

8. The process of claim 1, wherein the enzymatically treated starch further comprises amylopectin, partially debranched amylopectin, or a combination thereof.

9. The process of claim 1, wherein the process further comprises the step of blending the enzymatically treated starch with at least one other excipient selected for use in a wet granulation, dry granulation or direct compression tablet manufacturing process.

10. The process of claim 1 wherein the starch is enzymatically treated to debranch the starch and yield at least 60%, by weight, of the short chain amylose.

11. The process of claim 1 wherein the starch is enzymatically treated to debranch the starch and yield at least 75%, by weight, of the short chain amylose.

* * * * *

UNITED STATES PATENT AND TRADEMARK OFFICE
CERTIFICATE OF CORRECTION

PATENT NO. : 5,468,286
DATED : November 21, 1995
INVENTOR(S) : Wai-Chiu, et al

It is certified that error appears in the above-indentified patent and that said Letters Patent is hereby corrected as shown below:

On the title page, insert item

-- [62] Continuation-in-Part of Ser. No. 092,378, Jul. 15, 1993 which is a continuation of Ser. No. 427,065, Oct. 25, 1989. --

In Col. 1, after the title, insert:

-- This application is a continuation-in-part of U.S. Serial No. 08/092,378 filed July 15, 1993, now abandoned, which was a continuation application of U.S. Serial No. 07/427,065, filed October 25, 1989, now abandoned. --

Signed and Sealed this

Tenth Day of December, 1996

Attest:

BRUCE LEHMAN

*Attesting Officer*

*Commissioner of Patents and Trademarks*